United States Patent [19]

Baile et al.

[11] Patent Number: 4,855,469
[45] Date of Patent: Aug. 8, 1989

[54] PREPARATION OF CYCLOORGANOTRISILAZANES

[75] Inventors: Gnaneshwar R. Baile; John E. Herman; Geoffrey M. Wyshak, all of Midland, Mich.

[73] Assignee: Dow Corning Corporation, Midland, Mich.

[21] Appl. No.: 269,522

[22] Filed: Nov. 9, 1988

[51] Int. Cl.$^4$ .............................................. C07F 7/10
[52] U.S. Cl. ................................................... 556/409
[58] Field of Search ........................................ 556/409

[56] References Cited

U.S. PATENT DOCUMENTS

| 3,228,895 | 1/1966 | Burks et al. | 556/409 X |
| 3,414,584 | 12/1968 | Fink | 556/409 X |
| 3,518,289 | 6/1970 | Pearce et al. | 556/409 |
| 3,655,711 | 4/1972 | Bush et al. | 556/409 |
| 4,557,039 | 3/1986 | Arkles et al. | 556/409 |

FOREIGN PATENT DOCUMENTS 368267  1/1973  U.S.S.R. .............................. 556/409

OTHER PUBLICATIONS

Brewer et al., J. Am. Chem. Soc., vol. 70, p. 3888 (1948).

Primary Examiner—Paul F. Shaver
Attorney, Agent, or Firm—James E. Bittell

[57] ABSTRACT

What is disclosed is a process for the rearrangement of cylcoorganopolysilazanes to cycloorganotrisilazanes using quaternary ammonium halides as a catalyst. The quaternary ammonium halide has the formula $R^i_4NX$ where at least one $R^i$ is a group containing greater than 11 carbon atoms and X is a halogen atom. The rearrangement process is ran either as a batch or a continuous distillation procedure.

15 Claims, No Drawings 4,855,469

PREPARATION OF CYCLOORGANOTRISILAZANES

BACKGROUND OF THE INVENTION

This invention relates to the rearrangement of cycloorganopolysilazanes to cycloorganotrisilazanes. More specifically, this invention relates to preparation of cycloorganotrisilazanes using quaternary ammonium halides as a catalyst.

Silane blocking agents are used to replace active hydrogens with silyl groups. Replacement of active hydrogen with silyl groups often affords products which are more chemically stable and which undergo subsequent chemical reaction at sites other than the silyl blocked site. Hydrolysis of the silyl blocked site will subsequently regenerate the unprotected active hydrogen functionality. Difunctional silane blocking agents are available to selectively block primary amines, vic-diols and other difunctional sites, typically yielding 5-, 6-, and 7-member silicon-containing rings which are very stable to hydrolysis, oxidation and reduction. This process is termed cyclosilylation.

A useful technique for cyclosilylation is reaction with hexamethylcyclotrisilazane which forms stable blocked derivatives without formation of polymeric by-products and without need for bulky groups to be present on the substrate compound. This process has found wide use in the Pharmaceutical industry in the manufacture of such materials as steriods, salicylic, thiosalicylic, and anthranilic acids.

Cycloorganopolysilazanes may be prepared by the direct reaction of an organohalosilane with ammonia. Brewer, et al., J. Am. Chem. Soc., vol. 70, pg. 3888 (1948), discloses the preparation of cyclodimethylpolysilazanes from the reaction of dimethyldichlorosilane with ammonia. In the reaction of a diorganodihalosilane with ammonia, the reaction product is a mixture of cycloorganopolysilazanes. Many uses of cyclic silazanes prefer the cyclotrisilazane species.

Zhinkin, et al., U.S.S.R. SU. No. 368267, published Jan. 26, 1973, discloses a process for preparing hexamethylcyclotrisilazane via the catalytic rearrangement of octoamethylcyclotetrasilazane. The catalysts cited are ammonium sulfate, ammonium chloride, and sulfuric acid.

Arkles, et al., U.S. Pat. No. 4,557,039, issued Mar. 18, 1986, discloses a process for preparing cyclotrisilazanes by heating cyclotetrasilazanes in the presence of a Group VIII catalyst in the presence of hydrogen.

BRIEF SUMMARY OF THE INVENTION

The objective of the instant invention is a process for the preparation of cycloorganotrisilazanes via the rearrangement ofhigher homologs of cycloorganopolysilazanes. In the instant invention, it was found that quaternary ammonium halides with at least one long-chain pendant organic group were effective as a rearrangement catalyst. It was further found that these quaternary ammonium halides could facilitate the combined rearrangement, isolation, and recovery of the desired cycloorganotrisilazane.

The process described is for the preparation of a cycloorganotrisilizane having the formula, $(R_2SiNH)_3$, from a cycloorganopolysilazane having the formula, $(R_2SiNH)_y$, or mixtures thereof,
  wherein each R is independently selected from a group consisting of hydrogen, alkyl, alkenyl, aryl, and alkaryl; and yhas a value of 4 or greater.

The process further comprising heating the cycloorganopolysilazane in the presence of oa catalyst to form the cycloorganotrisilazane, said catalyst being selected from a group consisting of quaternary ammonium halides having the formula, $R^i_4NX$, wherein each $R^i$ is independently selected from a group consisting of alkyl, alkenyl, aryl, and alkaryl, and at least one $R^i$ is ag roup containing greater than 11 carbon atoms; and X is a halogen atom.

DETAILED DESCRIPTION OF THE INVENTION

The invention disclosed herein is a process for the preparation of cycloorganotrisilazanes via the rearrangement of higher homologs of cycloorganopolysilazanes in the presence of a quaternary ammonium halide catalyst.

For the cycloorganotrisilazane, $(R_2SiNH)_3$, and the prcursor cycloorganopolysilazane, $(R_2SiNH)_y$, each R can be hydrogen; alkyl, for example—$C_1$ to $C_{10}$ straight chain, branches, or cyclic aliphatic hydrocarbons; alkenyl, for example—$C_2$ and $C_{10}$ straight chain, branched, or cyclic unsaturated hydrocarbons; aryl or alkakryl groups, for example—phenyl, tolyl, naphtyl, or benzyl.

The cycloorganotrisilazane can be, for example—cyclohexamethyltrisilazane, cyclotriethyltrimethyl-trisilazane, cyclotrimethyltrivinyltrisilazane, cyclotrimethyl-tripphenyltrisiliazane, or cyclotri-n-hexyltribenzyltrisilazane.

The cycloorganopolysilazanes can be, for example, higher cyclic silazanes corresponding to the cyclic trimer silazanes, supra. As an example, for cyclohexamethyltrisilazane, the higher cyclic silazanes coul be cycloctamethyltetrasilazane, cyclodecamthylpentasiliazane, and so on. The cyclopolyorganosilazanes can also be a mixture of cyclic silalzanes with corresponding R groups, as for example, dimethyl, ethylmethyl, methylviny, or methylphenyl. While not limiting, preferred are cyclopolyorganosilzanes, $(R_2SiNH)_y$, or mixtures thereof in which y is 4 to 10.

For the quaternary ammonium halide, $R^i_4NX$, each $R^i$ may be selected froma group comprising an alkyl, for example—$C_1$ to $C_{30}$ linear or cyclic aliphatic hydrocarbons; an alkenyl, for example $C_2$ to $C_{10}$ linear or cyclic unsaturated hydrocarbons; and aryl or alkaryl groups, for example—phenyl, tolyl, naphtyl, or benzyl.

It has been found in the arrangement of cyclodimethylpolysilazanes that quaternary ammonium halides in which the pendant organic groups were only as high as $C_6$ resulted in little, if any, rearrangement to the desired cyclohexamethyltrisilazane. Quaternary ammonium halides in which one of the pendant organic groups was $C_{16}$ or $C_{18}$ were effective catalysts. In general, the inventors believe quaternary ammonium halides that have at least one pendant group of $C_{12}$ or higher will be effective catalysts. Preferred is a quaternary ammonium halide with one pendant group of $C_{12}$ or higher, and the remaining pendantn groups less than $C_{12}$ in size. The inventors theorize that the presence of teh $C_{12}$ or higher pendant group increases the solubility of the catalyst in cycloorganopolysilazanes, thereby making the catalyst more readily available to the reaction. However, it is not intended that the invention be limited by this theory which is advanced only as one possible explanation of the improved results obtained with the catalysts of this invention.

The quaternary ammonium halide can be for example dodecyltriethylammonium chloride, tetradecylvinyldimethylammonium iodide, hexadecyltrimethylammonium bromide, hexadecylphenyldimethylammonium bromide, or octadecylbenzyldimethylammonium chloride.

Preferred are quaternary ammonium halides which are stable at temperatures up to at least 90° C. Most preferred are quaternary ammonium halides which are stable at temperatures up to at least 150° C.

The amount of catalyst present in the reaction mixture is not critical to this invention. Generally, any amount of catalyst adequate to insure a sufficient rate of reaction is adequate. Preferred, is a catalyst concentration of 5-10 weight percent, of the reaction mixture. However, the optimum catalyst concentration may depend on the particular catalyst used.

The process of this invention can also be used as a multi-batch process wherein the cycloorganopolysilazanes, ($R_2SiNH$), in an organic solvent such as toluene, heptane, or hexane are combined with a quaternary ammonium halide that is stable to a temperature of at least 150° C. The solvent is initially stripped from the solution by heating at atmospheric pressure. The ($R_2SiNH$)$_y$ misture is then heated to a tempeature of at least 115° C. to about 150° C. at a reaction vessel pressure of less than 40 mm Hg and the ($R_2SiNH$)$_3$ is distilled from the reaction vessel with periodic replenishing of the cycloorganopolysilazanes. An example of a useful catalyst for this process is hexadecyltrimethylammonium bromide.

So that those skilled in the art may better understand and appreciate the instant invention, the following examples are presented.

These examples are presented to be illustrative and are not to be construed as limitingn the invention as claimed herein.

EXAMPLE 1 Hexamethylcyclotrisilazane was prepared by heating octamethylcyclotetrasilazane, (($CH_3$)$_2$SiNH)$_4$, in the presence of octadecylbenzyldimethylammonium chloride (ODBDMAC).

The ODBDMAC was prepared by the reaction of octadecyldimethylamine and benzyl chloride. In this preparation, 91.3 cc benzyl chloride and 246.5 cc octadecyldimethylamine were combined in the prsence of 1260 cc of dimethylformamide (DMF) as a solvent in a reaction vessel. The mixture was agitated and heated to a temperature of about 115° C. Samples of the mixture were taken and analyzed for percent chloride on nitrogen via Volhard titration. The reaction was analyzed to be abou 98 percent complete after about 41 hours of heating. Vacuum of about 80 mm Hg was applied to the mixture to remove the bulk of the DMF. The salt mixture was then filtered and dissolved in toluene to a concentration of about 20 weight percent salt in solution.

The rearrangement of (($CH_3$)$_2$SiNH)$_4$ was effected by first charging 132.1 g of octamethylcyclotetrasilalzane to a 2000 mL vessel. The cyclotetrasilalzane was heated to about 70° C. and 69.8 g of the above salt mixture was added. The concentration of ODBDMAC was calculated to be 7.4 weight percent. The mixture was maintained at a temperature of about 115° C. at atmospheric pressure. Samples of the mixture were taken during the course of then run and analyzed by gas chromatography (GC). Table 1 is a summary of the results of this run. In Table 1, the time after catalyst addition at which the samples were taken, reported in minutes, is denoted as "Time"; the GC results are reported as the ratio of cyclotrisilazane to cyclotetrasilazane content and denoted as "$S_3/S_4$."

TABLE 1

| Time | $S_3/S_4$ |
|---|---|
| 0 | 0.02 |
| 45 | 0.87 |
| 80 | 2.39 |
| 168 | 2.77 |
| 257 | 2.78 |
| 298 | 2.91 |
| 1380 | 3.26 |

The above results demonstrate that a quaternary ammonum halide is an effective catalyst for the conversion of cyclopolysilazanes to ocyclotrisilazanes.

EXAMPLE 2 Hexamethylcyclotrisilazanen was prepared by heating octamethylcyclotetrasilazane in the presence of a quaternary ammonium halide in a procedures similar to Example 1. The effect of ODBDMAC concentration was investigated.

The ODBDMAC was prepared in this sample using excess octadecyldimethylamine as a solvent in place of DMF. In this preparation, 1604.1 cc octadecyldimethylamine was heated in the presence of 132.0 cc benzyl chloride. The mixture was held at about 115C. and at atmospheric pressure. Sampling of the mixture and analysis for chlorine on nitrogen was carried out as in Example 1. After about 43 hours, the conversion of benzyl chloride was about 98 percent complete. Heating was discontinued and the salt mixture was collected.

Three separate rearrangement runs were made in which the concentration of the ODBDMAC was varied. The temperature for all three runs was maintained at about 115° C. Pressure atmospheric. Samples of the mixture were taken and analyzed by GC. Tables 2, 3, and 4 summarize the results of these three runs. The notation used is the same as that for Example 1. In addition, the concentration of the catalyst, expressed as weight percent of the mixture, for each run is included and denotd as "%Cat."

TABLE 2

| % Cat | Time | $S_3/S_4$ |
|---|---|---|
| 2.0 | 0 | 0.01 |
|  | 40 | 0.03 |
|  | 115 | 0.04 |
|  | 182 | 0.02 |
|  | 228 | 0.03 |

TABLE 3

| % Cat | Time | $S_3/S_4$ |
|---|---|---|
| 5.3 | 0 | 0.04 |

TABLE 3-continued

| % Cat | Time | S₃/S₄ |
|---|---|---|
| | 89 | 1.13 |
| | 130 | 2.23 |
| | 195 | 2.31 |
| | 260 | 2.29 |

TABLE 4

| % Cat | Time | S₃S₄ |
|---|---|---|
| 10.0 | 0 | 0.02 |
| | 120 | 1.58 |
| | 175 | 1.77 |
| | 225 | 2.26 |
| | 287 | 2.32 |
| | 1308 | 2.44 |

The above results demonstrate the impact of catalyst concentration on the conversion of ocyclopolysilazanes to cyclotrisilazanes.

EXAMPLE 3

Several quaternary ammonium halides were evaluated as catalysts for the conversion of cyclopolysilazanes to cyclotrisilazanes. The quaternary ammonium halides evaluated were hexadecyltrimethylammonium bromide (HDTMAB), tetraethylammonium bromide (TEAB), tetrapropyl ammonium bromide (TPAB), and phenyltrimethylammonium chloride (PTMAC).

Procedures and equipment similar to those used in Example 1 were utilized. In a typical run, 1273 g of solid octametthlcyclotetrasilazane and 63 g of HDTMAB were loaded into an agitated, heated reaction vessel. The mixture was heated to 150° C. Samples were taken hourly and analyzed by GC. In each run, catalyst concentration was 5 weight percent.

Table 5 is a summary of these runs. In Table 5, the time after catalyst addition, in hours, is designated "Time"; the quaternary ammonium halides are denoted as "HDTMAB", "TEAB", "TPAB", and "PTMAC"; and the hexamethylcyclotrisilazane content of the mixture denoted as "Percent S₃ Content."The S₃ concentration was calculated as a percent of total cyclic-silazanes in the mixture.

TABLE 5

| | Percent S₃ Content | | | |
|---|---|---|---|---|
| Time | HDTMAB | TEAB | TPAB | PTMAC |
| 1 | 1.1 | 0 | 2.5 | 1.2 |
| 2 | 1.5 | 0 | 2.5 | 1.3 |
| 3 | 2.8 | 0 | 2.4 | 1.3 |
| 4 | 6.7 | 0.8 | 2.5 | 1.4 |
| 5 | 15.0 | 0.9 | 2.4 | 1.3 |
| 6 | 29.3 | 0.9 | 2.5 | 1.3 |
| 7 | 51.5 | | | |

The above results demonstrate that under these reaction conditions not all quaternary ammonium halides effectively catalyze the rearrangement of cycloorganopolysilazanes to cycloorganotrisilazanes.

EXAMPLE 4 a multi-batch operation was carried out in which hexadecyltrimethylammonium bromide (HDTMAB) was used as a catalyst to facilitate conversion of octamethylcyclotetrasilazane (S₄) to hexamethylcyclotrisilazane (S₃).

Starting solutions were prepared by reacting dimethyldichlorosilane in hexane with ammonium and removing ammonium chloride by-product from the solution. The resultant solutions were typically about 80 to 85 weight percent hexane with the remainder comprising about 95 weightt percent S₃ and S₄. The ratio of S₃ to S₄ in these hexane solutions was typically about 0.6.

To a kettle, equipped with a packed distillation column, agitator, heating and cooling facilities, and a vacuum source was added HDTMAB. HDTMAB was added at about 5 weight percent of the initial S₃ plus S₄ concentration.

A first charge of the hexane solution was charged to the kettle. Hexane was stripped from the solution by heating to a temperature of about 120° C. at atmospheric pressure. Two additional charges of the hexane solution were similarly injected into the kettle, and hexane was stripped. A cut of distillate was taken off at a kettle temperature of from about 115° C. to 150° C. at a pressure of froma bout 35 to 50 mm Hg. The distillate was analyzed by gas chromatography to have an S₃/S₄ ratio of abou 182. A fourth and fifth charge of hexane solution were loaded to the kettle and S₃ was recovered as above.

About 85 percent of the S₃ and S₄ added to the kettle was recovered as cyclic-silazanes. S₃ constituted about 99 weight percent of the cyclic-silazanes recovered.

The above results demonstrate that a mixture of cyclicsilazanes can be converted to a high proportion of cyclotrisilazanes using a quaternary ammonium halide as a catalyst.

What is claimed is:

1. A process for the preparation of a cycloorganotrisilazane having the formula, $$(R_2SiNH)_3,$$ 

from a cycloorganopolysilazane having the formula, $$(R_2SiNH)_y,$$ 

or mixtures thereof,
wherein each R is independently selected from a group consisting of hydrogen, alkyl, alkenyl, aryl, and alkaryl, and y has a value of 4 or greater,
said process comprising heating the cycloorganopolysilazane in the presence of a catalyst to from the cycloorganotrisilazane, said catalyst being selected from a group consisting of quaternary ammonium halides, having the formula, $$R^i_4NX,$$ 

wherein each $R^i$ is independently selected from a group consisting of alkyl, alkenyl, aryl, and alkaryl, and at
least one $R^i$ is a group containing greater than 11 carbon atoms; and X is a halogen atom.

2. A process according to claim 1, wherein the cycloorganopolysilazane is heated in the presence of the catalyst at a temperature greater than about 90° C.

3. A process according to claim 2, further comprising separating and isolating the cycloorganotrisilazane.

4. A process according to claim 3, wherein separating and isolating the cycloorganotrisilazane is effected by distillation.

5. A process according to claim 4, wherein distillation of the cycloorganotrisilazane is effected as the cycloorganotrisilazane is forming.

6. A process according to claim 5, wherein the distillation of the cycloorganotrisilazane is conducted at a temperature of at least 100° C. to about 160° C. and a pressure of less than about 80 mm Hg.

7. A process according to claim 6, wherein the distillation of the cycloorganotrisilazane is conducted at a temperature of at least 115° C. to about 150° C. and a pressure of less than 40 mm Hg.

8. A process according to claim 7, wherein the catalyst is stable to a temperature of at least 150° C.

9. A process according to claim 8, wherein the catalyst is hexadecyltrimethylammonium bromide.

10. A process according to claim 7, wherein the catalyst is octadecyldimethylbenzylammonium chloride.

11. A process according to claim 7, wherein the cycloorganotrisilazane is cyclohexamethyltrisilazane and the cycloorganopolysilazane is cyclodimethylpolysilazane.

12. A process according to claim 2, wherein the cycloorganotrisilazane is cyclohexamethyltrisilazane and the cycloorganopolysilazane is cyclodimethylpolysilazane.

13. A process according to claim 12, wherein the catalyst is hexadecyltrimethylammonium bromide.

14. A process according to claim 12, wherein the catalyst is octadecyldimethylbenzylammonium chloride.

15. A process according to claim 12, wherein the catalyst is stable at a temperature greater than or equal to 90° C.

* * * * *